United States Patent
Talling et al.

(10) Patent No.: US 6,964,648 B2
(45) Date of Patent: Nov. 15, 2005

(54) DEVICE FOR INSERTING IMPLANTS

(75) Inventors: Christine Talling, Turku (FI); Esa Hallinen, Turku (FI)

(73) Assignee: Schering Oy, Turku (FI)

( * ) Notice: Subject to any disclaimer, the term of this patent is extended or adjusted under 35 U.S.C. 154(b) by 143 days.

(21) Appl. No.: 10/221,340

(22) PCT Filed: Mar. 7, 2001

(86) PCT No.: PCT/FI01/00224

§ 371 (c)(1), (2), (4) Date: Sep. 11, 2002

(87) PCT Pub. No.: WO01/68168

PCT Pub. Date: Sep. 20, 2001

(65) Prior Publication Data

US 2003/0040699 A1 Feb. 27, 2003

(30) Foreign Application Priority Data

Mar. 13, 2000 (FI) ................................ 20000572

(51) Int. Cl.$^7$ .................................... A61M 31/00
(52) U.S. Cl. ................. 604/60; 604/110; 604/218; 600/7
(58) Field of Search ................ 604/218, 110, 604/57–64; 600/1–15

(56) References Cited

U.S. PATENT DOCUMENTS

| | | | |
|---|---|---|---|
| 4,474,572 A | * 10/1984 | McNaughton et al. | ........ 604/61 |
| 4,664,654 A | 5/1987 | Strauss | ........................ 604/198 |
| 4,994,028 A | 2/1991 | Leonard et al. | ................ 604/60 |
| 5,290,235 A | 3/1994 | Polyblank et al. | ........... 604/110 |
| 5,558,637 A | 9/1996 | Allonen et al. | ................ 604/60 |
| 5,709,669 A | 1/1998 | Haining | ........................ 604/232 |

FOREIGN PATENT DOCUMENTS

| | | |
|---|---|---|
| EP | 0 515 710 | 12/1992 |
| EP | 0 539 634 | 5/1993 |
| EP | 0 596 162 | 5/1994 |
| EP | 0 858 813 | 8/1998 |
| RU | 2126274 | 2/1999 |
| WO | WO 96/09849 | 4/1996 |
| WO | WO 99/33512 | 7/1999 |
| WO | WO 99/42148 | 8/1999 |

* cited by examiner

Primary Examiner—Kevin C. Sirmons
(74) Attorney, Agent, or Firm—James C. Lydon

(57) ABSTRACT

A disposable device for inserting one or more implants, the device including a tublar cannula (10) having a tip (11), the cannula also serving as a container for the implants, a plunger (20) and a handle (30) having a first end (31) directed towards the cannula, and a second end (32) directed away from the cannula. The plunger and handle are attached or attachable to each other in fixed manner, and the cannula is arranged to be movable in the longitudinal direction, so that the plunger is placed within. The cannula can, after inserting the implant or implants, be drawn on top of the plunger (20) so far that tip (11) becomes covered by handle (30) or by a piece connected to handle (30), and/or cannula (10) is, when drawn to its extreme position, towards second end (32) of handle (30), arranged to be irretrievably locked in relation to plunger (20).

5 Claims, 3 Drawing Sheets

DEVICE FOR INSERTING IMPLANTS

Figure 1:
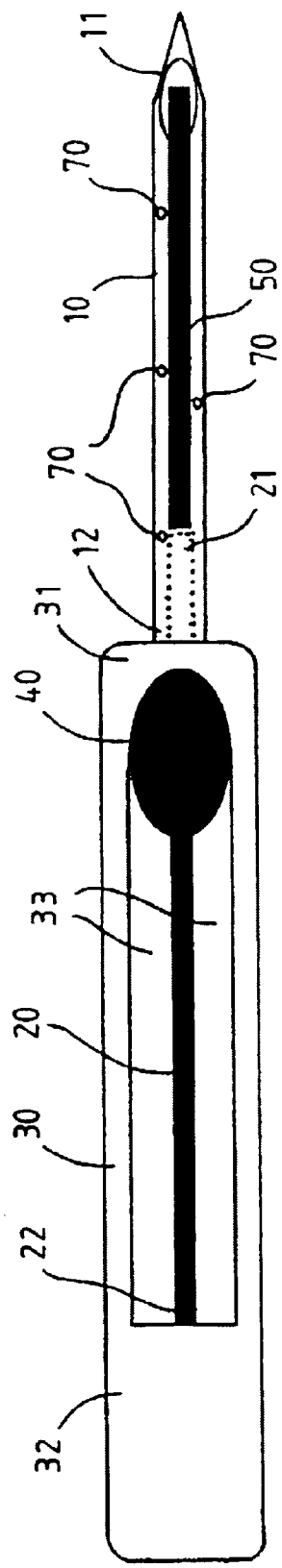

This application is a U.S. National Stage of International application PCT/FI01/00224, filed Mar. 7, 2001 and published on Sep. 20, 2001 in the English Language.

The invention relates to a disposable device for inserting implants.

Syringes designed for inserting implants are described in patent literature. For instance the patent publications EP 304700, EP 304107, WO 8806905, U.S. Pat. Nos. 4,451,254, 4,820,267 and GB 2199247 describe various devices for inserting implants. The patent EP 304700 describes a device where the sterility is improved by preventing the plunger from accidentally falling off the housing. The housing is made of plastic, but the cannula and the plunger are made of metal. The patent EP 304107 introduces a disposable device for inserting implants, where the housing is made of plastic, but the cannula is made of metal. In particular said patent relates to a structure provided in connection with the plunger, whereby the implant is prevented from being pushed forward too early, i.e. when the skin is being penetrated. The published international application WO 8806905 relates to a complex device designed for repeated use for inserting several successively positioned implants in the syringe subcutaneously in a desired manner. In particular, this invention relates to an arrangement for inserting said implants. The U.S. Pat. No. 4,451,254 likewise describes a device designed for repeated use for inserting a plurality of implants, where the implants are fed from an implant cartridge installed at the side of the syringe. The publication GB 2199247 describes a syringe for inserting hormonal implants, which syringe is completely made of plastic, and meant for single use only.

The published international application WO 9510314 describes an all-plastic device for inserting implants; said device includes a separate, protected incision blade, which after use can also be protected by means of a structure provided in the device. Owing to the cooperating elements provided in the plunger and the implant housing, the plunger cannot be drawn out of the housing after the device has been used, which effectively prevents any further usage of the device. However, the described device requires the use of both hands while inserting.

The object of the invention is to provide a new disposable device for inserting implants, which device is safe to operate and to destroy after use, both in respect of hurting or infecting oneself.

Another object of the invention is to provide an advanced, disposable device for inserting implants, which device is effectively prevented from being reused.

Yet another object of the invention is to provide a device whereby one or several implants can be inserted subcutaneously quickly and easily, by using only one hand in the operation.

Consequently, the object of the invention is a disposable device for inserting one or several implants, said device comprising a tubular cannula provided with a tip, which cannula also serves as a container for the implants, a plunger, and a handle with a first end directed to the cannula and a second end directed away from the cannula, wherein the plunger and the handle are attached or attachable to each other in a fixed manner, and that the cannula is arranged to be movable in the longitudinal direction, so that the plunger is positioned inside the cannula.

The invention is characterized in that i) the cannula can, after inserting the implant or implants, be drawn on top of the plunger so far, that the tip of the cannula is covered by the handle or a piece connected to the handle, and/or that ii) the cannula is, when drawn to the extreme position towards the second end of the handle, arranged to be irreversibly locked with respect to the plunger.

Figure 2:
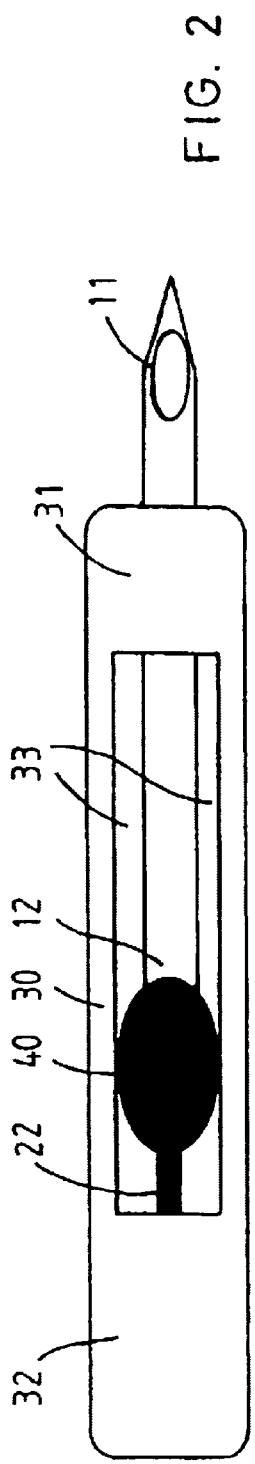
Figure 3:
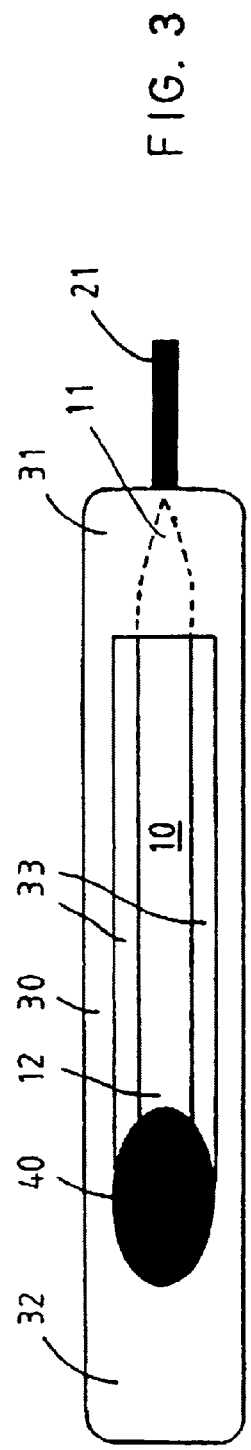
Figure 4:
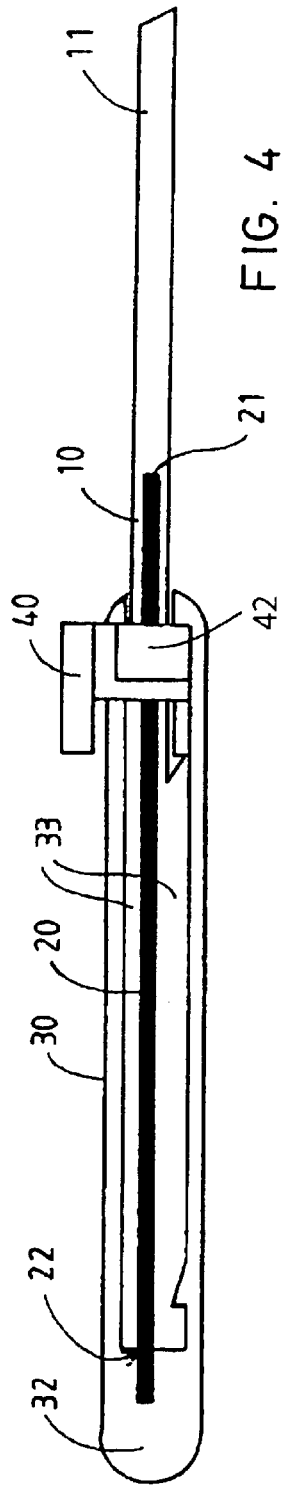
Figure 5:
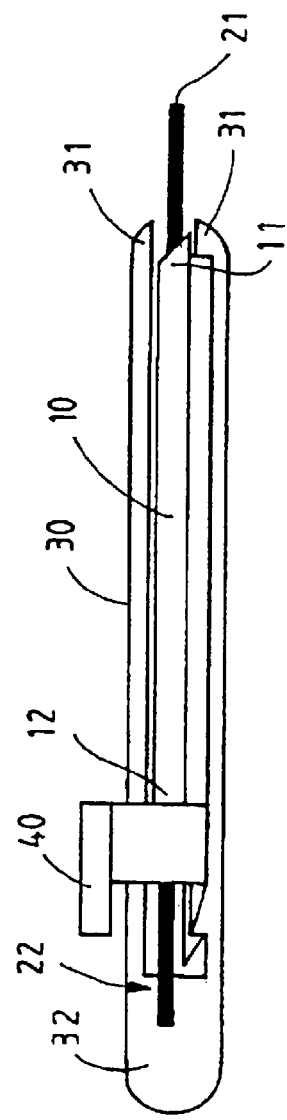
Figure 8:
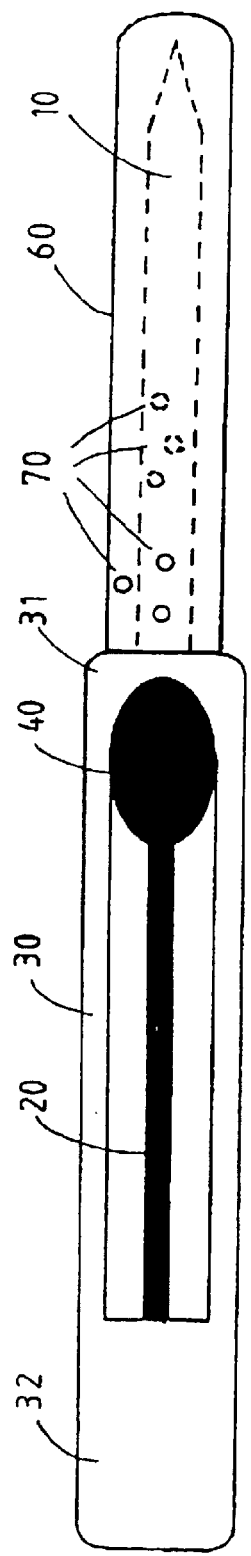
Figure 6:
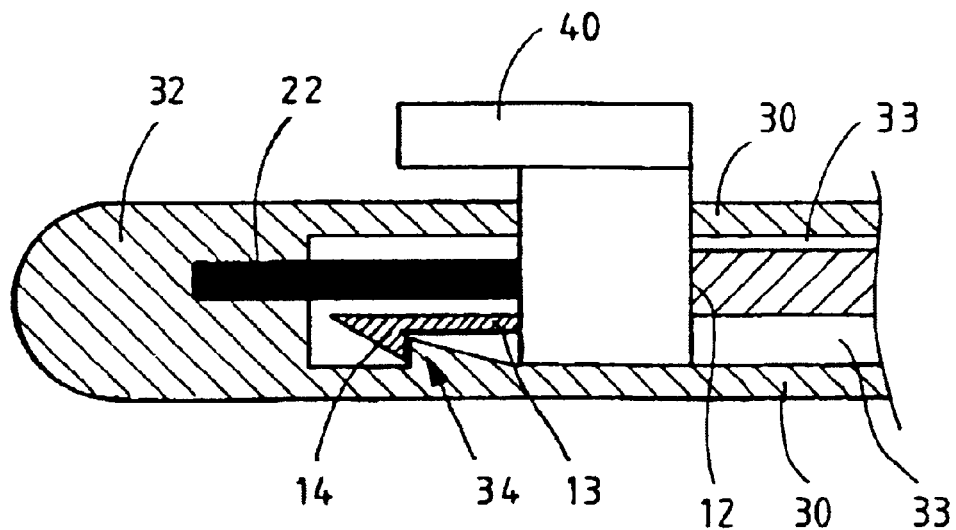
Figure 7:
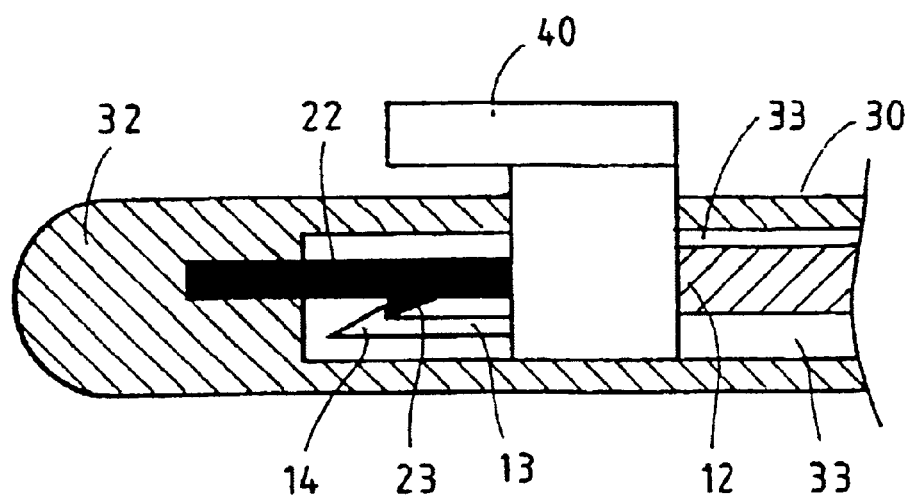

The invention is described in more detail with reference to the appended drawings, where FIG. 1 is a top-view illustration of a device according to the invention, seen in full readiness for use, FIG. 2 illustrates the device of FIG. 1, seen immediately after inserting the implant/implants, FIG. 3 illustrates the device of FIG. 1, seen in the end position after use, FIG. 4 illustrates the device of FIG. 1 ready for use, seen in a side-view cross-section, FIG. 5 illustrates the device of FIG. 4 in the end position after use, FIG. 6 illustrates a detail of the locking mechanism shown in FIG. 5, FIG. 7 illustrates an alternative locking mechanism, and FIG. 8 illustrates the device of FIG. 1, provided with a protective cap.

FIG. 1 is a top-view illustration of a device according to the invention in full readiness for use. The device includes a tubular cannula 10 provided with a tip 11, said cannula also serving as a container for implants. From the figure it is seen that the cannula contains an implant 50 ready to be inserted underneath the skin of an individual. In principle, the cannula could also contain several successively positioned implants. The device further includes a plunger 20 and a handle 30, provided with a first end marked with reference numeral 31, directed towards the cannula 10, and with a second end marked with reference numeral 32, directed away from the cannula. The plunger 20 and the handle 30 are attached to each other in a fixed manner. From FIG. 1 it can be seen that the plunger's end 21 directed towards the cannula is extended to outside the first end 31 of the handle, i.e. it is inserted to the cannula and supports the implant contained therein. The cannula 10 is arranged to be movable in the longitudinal direction, surrounding the plunger 20, so that when moving the cannula 10 towards the second end 32 of the handle 30, the free end 21 of the plunger 20 makes contact with the implant contained in the cannula. When the cannula is in this position, the device is ready for use.

From FIG. 2, which illustrates the device after inserting the implant, it is seen that the cannula 10 is in the longitudinal direction movable in the direction of the arrow, so that the plunger 20 remains inside the cannula. In the arrangements described in the drawings, the handle 30 is provided with a channel 33 proceeding in the longitudinal direction of the plunger, in which channel the plunger 20 is fitted in a fixed manner. The channel 33 allows for the longitudinal motion of the cannula 10. In order to facilitate the moving of the cannula 10, that end 12 of the cannula that is directed away from the cannula tip 11 is provided with a knob 40.

The device is used as follows: an incision is made in the patient's skin by means of the cannula's own tip 11 or by means of a separate blade. Thereafter the cannula, with the implants therein, is inserted underneath the skin. By applying the arrangement illustrated in the drawings, the device can be easily operated by one hand. The device is held by the handle while penetrating the skin by the cannula. At the insertion step of the implant, the cannula is drawn back, towards the holding hand, by gripping the knob 40 by the thumb of the same hand.

In FIG. 3, the cannula 10 is, after inserting the implant, drawn on top of the plunger 20, so far back (i.e. towards the handle end 32), that the cannula tip 11 remains completely in the protection of the handle 30. Owing to this structure, the device is safer to handle after use than the prior art insertion devices. The risk that the tip should cut wounds to the user and/or that possible blood drops left at the tip should spread infections is eliminated by this arrangement.

In FIG. 5, where the device according to the invention is illustrated from the side, it is seen that when the cannula is drawn to its extreme position towards the second handle end 32, the cannula is locked in the handle 30 and therethrough also with respect to the plunger 20. The locking, which is seen in more detail in FIG. 6, is such that the cannula cannot be pushed further forward so that the tip 11 will come out of the protection of the handle 30, without breaking the device. This structure further improves the operational safety of the device, because the sharp tip 11 remains irreversibly inside the handle. Said structure further ensures that the device cannot be reused.

The structure of the locking mechanism illustrated in FIG. 5 is shown in more detail in FIG. 6. At the end 12 of the cannula 10, there is arranged a bracket 13 provided with a barbed hook 14. At the handle end 32, there is formed a barbed hook 34 extending to inside the channel 33. When the cannula 10 is moved towards the handle end 32, the barbed hook 14 slides over the barbed hook 34 owing to the flexibility of the bracket 13. Thereafter the elements 14 and 34 are locked to each other, so that it is impossible to move the cannula towards the tip.

FIG. 7 shows another arrangement, where at the end 22 of the plunger 20 that is directed away from the cannula tip 11, there is arranged a barbed hook 23, which in cooperation with the barbed hook 14 causes the locking.

When the device is ready for use according to FIG. 1, and the implant rests against the plunger end 21, it is recommendable that the position of the cannula in relation to the plunger is locked in order to prevent the implant from being released prematurely. The described retrievable locking can for example be a separate locking member, which can easily be removed. See, for example, means 42 for reversibly locking the cannula, depicted in FIG. 4. As an alternative, the locking can be a spring-loaded press button or the like, which can easily be set on and off by clicking. If the cannula contains several implants, it may be suitable that the spring-loaded locking system is automatically activated after inserting each implant. In case the user wishes to inject the next implant beside the first one and not in succession thereto, he may turn the device somewhat without any risk of inserting the second implant prematurely. When the device is in the correct position, the user releases the locking system and inserts the implant by pulling the cannula towards the hand.

The motion of the cannula can also be guided by means of marks, for instance lines, made in the handle and/or in the cannula. In case the device is meant for a plurality of implants, the handle and/or the cannula is suitably provided with one mark per each implant.

The cannula 10 of the device is suitably protected by a separate protecting cap 60 (FIG. 8). The protecting cap is detached before using the device.

The device that is ready for use and suitably packed in a protective package, complete with the implants contained therein, is sterilized for example by irradiation or by gas. In case the sterilization is carried out by gas, it is recommendable that the cannula 10 and the possible protecting cap 60 are provided with apertures 70 that permeate the sterilizing gases (FIGS. 1 and 8).

The cannula of the device can be made of any suitable material. According to one alternative, the cannula 10 and the tip 11 thereof together constitute a uniform piece made of metal. As an alternative, the tubular part of the cannula 10 is made of plastic wherein a metallic tip 11 is attached. According to another alternative, the cannula complete with the tip constitutes one single piece made of plastic. In this case, there is probably needed a separate instrument for breaking the skin of the patient. Consequently, an incision blade can be connected to the protecting cap 60 or handle 30 of the device in a way described in the patent publication WO 95/10314. In that case in the vicinity of the incision blade, there is arranged a protective bracket for protecting the blade. Said bracket can be provided with a slot in which the used blade can be inserted according to FIGS. 6–8 of said patent publication.

In the above described arrangements, the handle is an object provided with an open channel. As an alternative, the handle could be a tubular object wherein the plunger is fitted, in which case in between the plunger and the inner surface of the tubular object, there is left room for the motion of the cannula. In the wall of the tubular object, there is arranged a longitudinal slot for the motion of a knob extending to outside the tube wall and attached to the cannula. This principle is introduced for instance in the U.S. Pat. No. 4,820,267, in FIG. 2. However, a handle provided with an open channel may be recommendable, because the structure is simpler, and the device is easier to operate with one hand.

The above-mentioned embodiments of the invention are only examples of how the idea according to the invention can be realized. For a man skilled in the art, it is obvious that the various embodiments of the invention can be modified within the scope of the appended claims.

We claim:

1. A disposable device for inserting one or several implants, said device comprising
    a tubular cannula provided with a tip, said cannula also serving as a container for the implants,
    a plunger and
    a handle having a first end directed towards the cannula, and second end directed away from the cannula,
    wherein said plunger and handle are attached or attachable to each other in fixed manner, and said cannula is arranged to be movable in the longitudinal direction, so that the plunger is placed inside the cannula, and wherein
    i) the cannula can, after inserting the implant or implants, be drawn on top of the plunger so far, that the tip of the cannula becomes covered by the handle or by a piece connected to the handle, and
    ii) the cannula is, when drawn to its extreme position towards the second end of the handle, arranged to be irretrievably locked with respect to the plunger, and wherein
    the handle is provided with a channel proceeding in the longitudinal direction thereof, which channel allows the cannula to move in the longitudinal direction, and that the end directed away from the tip of the cannula is provided with a knob, further comprising means for reversably locking the cannula when an implant rests against an end of said plunger.

2. The device of claim 1, wherein the device is provided with a protecting cap for protecting the cannula.

3. The device of claim 1, wherein the cannula and optionally a protecting cap are provided with apertures permeable to sterilizing gases.

4. The device of claim 1, wherein the tip of the cannula is made of metal, and optionally the cannula itself is also made of metal.

5. A disposable device for inserting one or several implants, said device comprising
- a tubular cannula provided with a tip, said cannula also serving as a container for the implants,
- a plunger and
- a handle having a first end directed towards the cannula, and a second end directed away from the cannula,
- a means for reversably locking the cannula when an implant rests against an end of said plunger wherein said plunger and handle are attached or attachable to each other in fixed manner, and said cannula is arranged to be moveable in the longitudinal direction, so that the plunger is placed inside the cannula, and wherein the cannula is, when drawn to its extreme position towards the second end of the handle, arranged to be irretrievably locked with respect to the plunger, wherein

- the handle is provided with a channel proceeding in the longitudinal direction thereof, which channel allows the cannula to move in the longitudinal direction, and that the end directed away from the tip of the cannula is provided with a knob.

* * * * *